(12) United States Patent  
Nolting et al.

(10) Patent No.: US 6,488,701 B1  
(45) Date of Patent: Dec. 3, 2002

(54) STENT-GRAFT ASSEMBLY WITH THIN-WALLED GRAFT COMPONENT AND METHOD OF MANUFACTURE

(75) Inventors: John E. Nolting, Santa Rosa, CA (US); Michael S. Williams, Santa Rosa, CA (US); Matthew J. Birdsall, Santa Rosa, CA (US); Robert D. Lashinski, Sebastopol, CA (US); Samuel L. Shull, Santa Rosa, CA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 09/053,145

(22) Filed: Mar. 31, 1998

(51) Int. Cl.[7] .................................................. A61F 2/06
(52) U.S. Cl. ................... 623/1.13; 623/1.23; 623/1.39; 623/1.46; 623/1.15
(58) Field of Search .............................. 623/1.13, 1.15, 623/1.23, 1.39, 1.46

(56) References Cited

U.S. PATENT DOCUMENTS

| | | | |
|---|---|---|---|
| 4,731,073 A | 3/1988 | Robinson | 623/1 |
| 4,776,337 A | 10/1988 | Palmaz | 128/343 |
| 5,123,917 A | 6/1992 | Lee | 623/1 |
| 5,207,960 A | 5/1993 | Moret de Rocheprise | 264/103 |
| 5,282,823 A | 2/1994 | Schwartz | 606/198 |
| 5,282,860 A | 2/1994 | Matsuno et al. | 623/12 |
| 5,330,500 A | 7/1994 | Song | 606/198 |
| 5,360,443 A | 11/1994 | Barone et al. | 623/1 |
| 5,389,106 A | 2/1995 | Tower | 606/198 |
| 5,443,496 A | 8/1995 | Schwartz et al. | 623/1 |
| 5,449,382 A | 9/1995 | Dayton | 623/1 |
| 5,489,295 A | 2/1996 | Piplani | 623/1 |
| 5,507,717 A | 4/1996 | Gianturco | 606/198 |
| 5,522,880 A | 6/1996 | Barone et al. | 623/1 |
| 5,522,882 A | 6/1996 | Gaterud et al. | 623/1 |

(List continued on next page.)

FOREIGN PATENT DOCUMENTS

| | | |
|---|---|---|
| EP | 0 466 518 A2 | 1/1992 |
| EP | 0 556 850 A1 | 8/1993 |
| EP | 0 621 016 A1 | 10/1994 |
| EP | 0 657 147 A3 | 6/1995 |
| EP | 0 686 379 A2 | 12/1995 |
| EP | 0 689 805 A3 | 3/1996 |
| EP | 0 701 800 A1 | 3/1996 |
| EP | 0 712 614 A1 | 5/1996 |
| EP | 0 747 020 A3 | 11/1996 |
| EP | 0 797 963 A2 | 1/1997 |
| EP | 0 775 472 A2 | 5/1997 |
| WO | WO 84/03036 | 8/1984 |
| WO | WO 95/05132 | 2/1995 |
| WO | WO 96/14808 | 5/1996 |
| WO | WO 96/21404 | 7/1996 |
| WO | WO 96/39104 | 12/1996 |

OTHER PUBLICATIONS

Jomed Internet Advertisement, "Jostent Coronary Stent Graft—The Best of Two Worlds", http://www.jomed.com/docs/graftl.htm, Oct. 16, 1997.

Primary Examiner—Corrine McDermott
Assistant Examiner—Cheryl Miller

(57) ABSTRACT

A stent-graft assembly having a thin-walled membrane and method of preparing the same are disclosed. In a first embodiment, the assembly comprises a stent, a coating and a porous membrane, wherein the membrane is less than 0.040 inch thick or less. Portions of the coating extend into the pores of the thin membrane to sealingly engage the membrane to achieve secure adhesion. In a second embodiment the coating and thin membrane bond to form a homogenous structure. In an alternative embodiment, the assembly comprises an inner and outer thin membrane bound to one another through the interstices of the support member and a coating at the proximal and distal regions. In any of the foregoing embodiments, the proximal and distal regions of the stent-graft assembly may comprise an additional coating, whereby layers of material are sealed, thereby minimizing thrombogenic potential of free ends of the assembly.

11 Claims, 7 Drawing Sheets

U.S. PATENT DOCUMENTS

| | | | |
|---|---|---|---|
| 5,534,287 A | 7/1996 | Lukic | 427/2.25 |
| 5,556,414 A | 9/1996 | Turi | 606/198 |
| 5,562,728 A | 10/1996 | Lazarus et al. | 623/1 |
| 5,571,173 A | 11/1996 | Parodi | 623/1 |
| 5,578,071 A | 11/1996 | Parodi | 623/1 |
| 5,578,072 A | 11/1996 | Barone et al. | 623/1 |
| 5,628,785 A | 5/1997 | Schwartz et al. | 623/1 |
| 5,628,786 A | 5/1997 | Banas et al. | 623/1 |
| 5,628,788 A | 5/1997 | Pinchuk | 623/1 |
| 5,632,772 A | 5/1997 | Alcime et al. | 623/1 |
| 5,637,113 A | 6/1997 | Tartaglia et al. | 623/1 |
| 5,639,278 A | 6/1997 | Dereume et al. | 623/1 |
| 5,641,373 A | 6/1997 | Shannon et al. | 156/242 |
| 5,645,559 A | 7/1997 | Hachtman et al. | 606/198 |
| 5,653,743 A | 8/1997 | Martin | 623/1 |
| 5,653,747 A | 8/1997 | Dereume | 623/1 |
| 5,667,523 A | 9/1997 | Bynon | 606/198 |
| 5,674,241 A | 10/1997 | Bley et al. | 606/198 |
| 5,683,448 A | 11/1997 | Cragg | 623/1 |
| 5,683,453 A | 11/1997 | Palmaz | 623/1 |
| 5,693,085 A * | 12/1997 | Buirge et al. | 606/192 |
| 5,700,285 A | 12/1997 | Myers et al. | 623/1 |
| 5,713,917 A | 2/1998 | Leonhardt et al. | 606/194 |
| 5,723,004 A | 3/1998 | Dereume et al. | 623/1 |

* cited by examiner

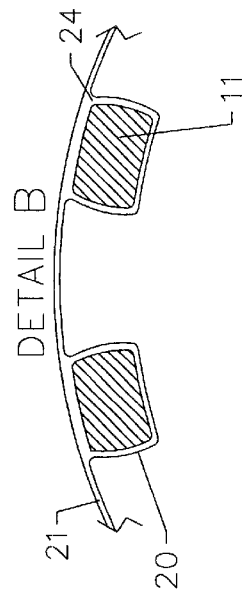
FIGURE 4B
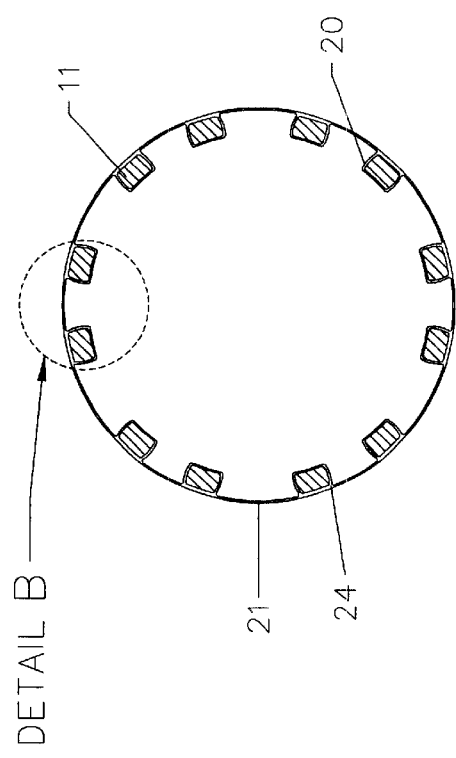
FIGURE 4A
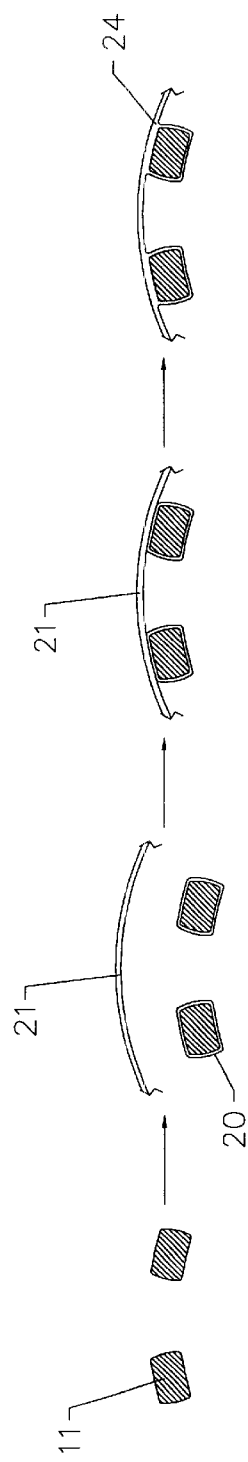

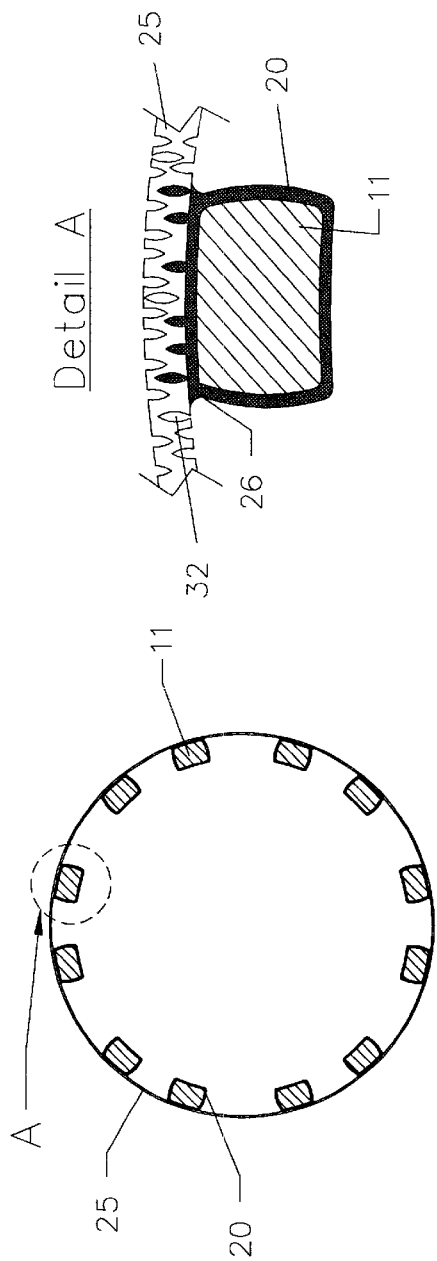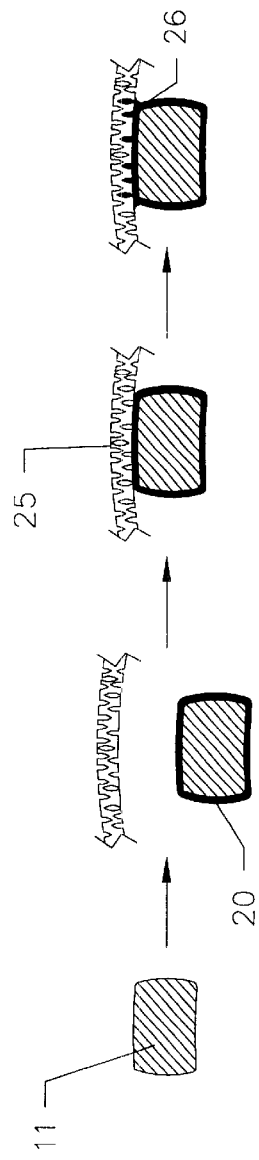

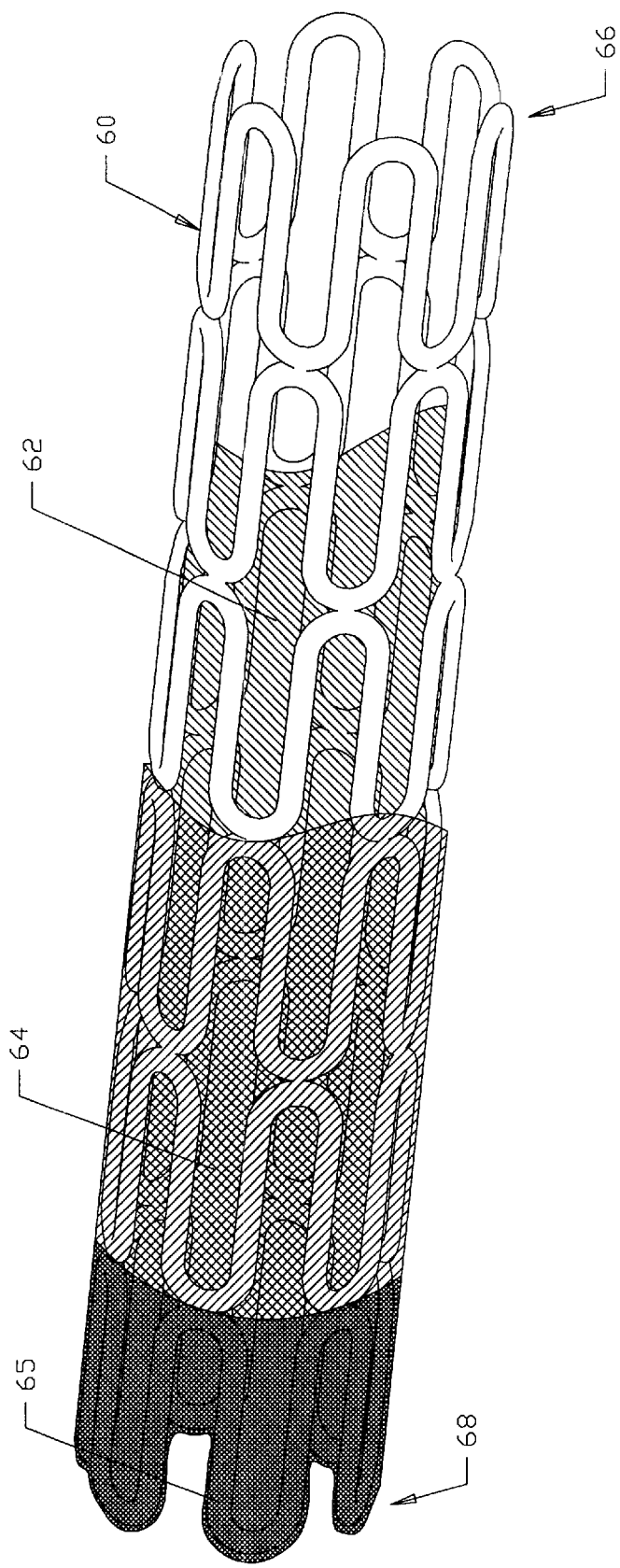

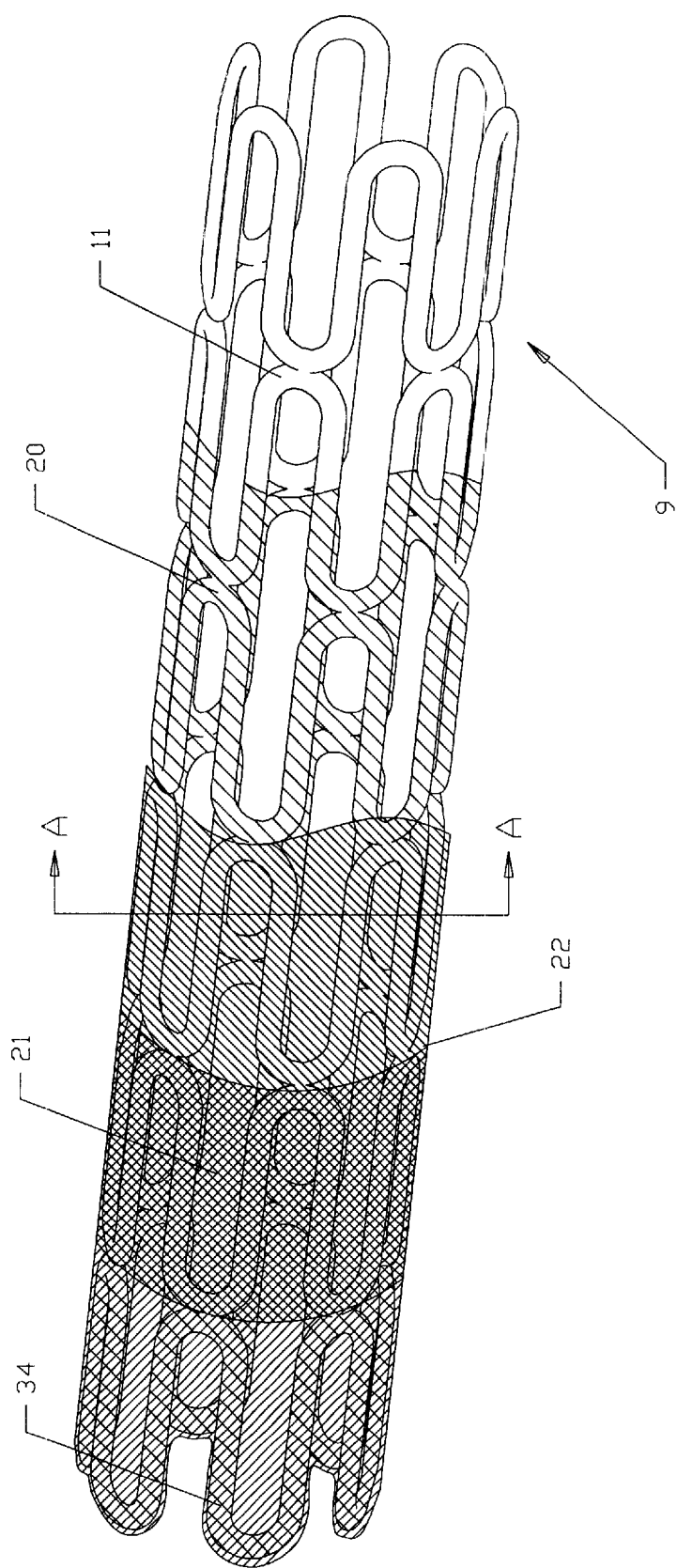

STENT-GRAFT ASSEMBLY WITH THIN-WALLED GRAFT COMPONENT AND METHOD OF MANUFACTURE

FIELD OF THE INVENTION

The present invention relates generally to endoluminal grafts for stenotic or diseased lumens and methods of making such grafts. More particularly, the invention includes a stent-graft assembly comprising a thin-walled graft component and methods of making the assembly.

BACKGROUND OF THE INVENTION

A wide range of medical treatments have been previously developed using "endoluminal prostheses," which terms are herein intended to mean medical devices which are adapted for temporary or permanent implantation within a body lumen, including both naturally occurring or artificially made lumens. Examples of lumens in which endoluminal prostheses may be implanted include, without limitation: arteries, such as those located within the coronary, mesentery, peripheral, or cerebral vasculature; veins; gastrointestinal tract; biliary tract; urethra; trachea; hepatic shunts; and fallopian tubes. Various types of endoluminal prostheses have also been developed, each providing a uniquely beneficial structure to modify the mechanics of the targeted luminal wall.

For example, various grafts, stents, and combination stent-graft prostheses have been previously disclosed for implantation within body lumens. More specifically regarding stents, various designs of these prostheses have been previously disclosed for providing artificial radial support to the wall tissue which forms the various lumens within the body, and often more specifically within the blood vessels of the body. An example of such a stent displaying optimal radial strength includes, but is not limited to, the stent disclosed in U.S. Pat. No. 5,292,331 to Boneau, the disclosure of which is herein incorporated by reference. Stents of other designs are known in the art, and may also be suitable for use in the stent-graft assembly. Other example of stents include but are not limited to those disclosed in U.S. Pat. No. 4,733,665 issued to Palmaz, U.S. Pat. No. 5,195,984 issued to Schatz, or U.S. Pat. No. 5,514,154 issued to Lau. Stents are used alone or in conjunction with grafts.

The use of an angioplasty balloon catheter is common in the art as a minimally invasive treatment to enlarge a stenotic or diseased blood vessel. This treatment is known as percutaneous transluminal angioplasty, or PTA. To provide radial support to the treated vessel in order to prolong the positive effects of PTA, a stent may be implanted in conjunction with the procedure. Under this procedure, the stent may be collapsed to an insertion diameter and inserted into a body lumen at a site remote from the diseased vessel. The stent may then be delivered to the desired site of treatment within the affected lumen and deployed to its desired diameter for treatment. Although the stents listed above are balloon expandable, stents which rely on other modes of deployment such as self-expansion, may be used to make a device according to the present invention. Because the procedure requires insertion of the stent at a site remote from the site of treatment, the device must be guided through the potentially tortuous conduit of the body lumen to the treatment site. Therefore, the stent must be capable of being reduced to a small insertion diameter and must be flexible.

During an angioplasty procedure, atheromatous plaques undergo fissuring, thereby creating a thrombogenic environment in the lumen. Excessive scarring may also occur following the procedure, potentially resulting in reocclusion of the treated lumen. Attempts to address these problems include providing a suitable surface within the lumen for more controlled healing to occur in addition to the support provided by a stent. These attempts include providing a lining or covering in conjunction with an implanted stent. A stent with such a lining or covering is known in the art as a stent-graft.

The graft component, or membrane, of a stent-graft may prevent excessive tissue prolapse or protrusion of tissue growth through the interstices of the stent while allowing limited tissue in-growth to occur to enhance the implantation. The surface of the graft material at the same time may minimize thrombosis, prevent scarring from occluding the lumen, prevent embolic events and minimize the contact between the fissured plaque and the hematological elements in the bloodstream.

A combination stent-graft may serve other objectives, such as delivering therapeutic agents via the assembly, excluding aneurysms or other malformations, occluding a side branch of a lumen without sacrificing perforator branches, conferring radiopacity on the device, and others. Various designs to achieve these objectives include stents partially or completely coated or covered with materials, some of which are impregnated with therapeutic agents, radiopaque elements, or other features designed to achieve the particular objectives of the device.

A graft component may be combined with a stent in order to achieve some or all of the foregoing objectives. However, adding a graft layer to the stent increases the challenges of delivering a stent via a catheter by increasing the crossing profile, or diameter, of the device, and by decreasing the flexibility of the device. Because the angioplasty process requires the insertion of the device into a body lumen at a site remote from the site of treatment and the guiding of the device the body lumen to the treatment site, it is required that the device be both capable of being collapsed to a relatively small diameter and be quite flexible. Moreover, flexibility and a desirable insertion diameter must be achieved without sacrificing the treatment objectives of the assembly, which include, at a minimum, radial strength. Therefore, an objective of a combination stent and graft is achieving the advantages of both a stent and a graft without significantly increasing the crossing profile of the device or significantly decreasing the flexibility of the device.

Various methods of manufacturing graft devices alone have been disclosed in the art. One such method for manufacturing a graft is disclosed in U.S. Pat. No. 5,641,373, issued to Shannon et al. The disclosed method comprises reinforcing an extruded flouropolymer tube with a second flouropolymer tube. The second tube is prepared by winding fluoropolymer tape around the exterior of a mandrel and heating it to form a tube. The graft may then be mounted on an anchoring mechanism such as a stent or other fixation device.

Another example of a graft is disclosed in U.S. Pat. No. 4,731,073, issued to Robinson. The graft disclosed therein comprises multiple layers of segmented polyether-polyurethane which form multiple zones having varying porosities.

U.S. Pat. No. 5,628,786, issued to Banas, discloses a polytetrafluoroethylene (PTFE) graft which has a reinforcing structure integrally bound to the graft. The reinforcing structure may be in the form of a rib which is sintered or otherwise integrally bound to the graft.

U.S. Pat. No. 5,207,960, issued to Moret de Rocheprise, discloses a process for the manufacture of a thin-walled tube of fluorinated resin tape. The method includes winding the tape around a mandrel and sintering the tape. While still on the mandrel, the tube is rolled to elongate the tube, to reduce the thickness of the tube, and to facilitate removal of the tube from the mandrel. The patent discloses that the tubes obtained can be used particularly as sheaths for the lining of metal tubes.

There are also numerous examples of combination stent-grafts disclosed in the art. U.S. Pat. No. 5,653,747 issued to Dereume discloses a stent to which a graft is attached. The graft component is produced by extruding polymer in solution into fibers from a spinnerette onto a rotating mandrel. A stent may be placed over the fibers while on the mandrel and then an additional layer of fibers spun onto the stent. The layer or layers of fibers may be bonded to the stent and/or one another by heat or by adhesives.

PCT Application WO 95/05132 discloses a stent around which a thin film of PTFE has been wrapped circumferentially one time and overlapped upon itself to form a seam. The stent may be alternatively or additionally placed to cover the interior of the stent. Fluorinated ethylene propylene is used as an adhesive to affix the graft to the stent.

A specific example of a coated stent is disclosed by Pinchuk in European Patent Application EP 0 797 963 A2. The objectives of Pinchuk's invention include both increasing the hoop strength and decreasing the thrombogenic potential of a criss-crossed wire stent or a zig-zag stent. Pinchuk's application also discloses covering the coated stent in the manner disclosed in U.S. patent application Ser. No. 5,653,747 issued to Dereume, discussed above.

An example of a stent and tubular graft is disclosed in U.S. Pat. No. 5,522,882 issued to Gaterud, et al. Gaterud discloses an expandable stent mounted on a balloon and a graft mounted over the stent.

U.S. Pat. No. 5,123,917 issued to Lee discusses a flexible and expandable inner tube upon which separate ring scaffold members are mounted, and a flexible and expandable outer tube enclosing the inner tube and scaffold members. The rings may be secured to the inner liner with an adhesive layer. Alternatively, the liners may be adhered to each other with the rings trapped between the layers. Lee discloses that the luminal surface of the device may be coated with various pharmacological agents.

Similarly, U.S. Pat. Nos. 5,282,823 and 5,443,496, both issued to Schwartz, et al. disclose a stent with a polymeric film extending between the stent elements, and strain relief means in the form of cuts in the film to allow the stent to fully expand and conform to the interior of the lumen. The thin polymeric film is applied to the stent while in solution and dried. Once dried, cuts are made in the film to provide strain relief means.

Another assembly includes a stent embedded in a plastic sleeve or stitched or glued to a nylon sleeve, as in U.S. Pat. No. 5,507,771, issued to Gianturco. Other prior art devices requiring stitching of the graft to the stent are disclosed in European Patent Application EP 0 686 379 A2, which teaches a perforate tubular frame having a fabric liner stitched to the frame, and World Intellectual Property Organization Application Number WO 96/21404 which indicates that the graft be stitched to the stent, and possibly to loops or eyelets which are part of the stent structure.

U.S. Pat. No. 5,637,113 issued to Tartaglia teaches a stent with a sheet of polymeric film wrapped around the exterior. Tartaglia teaches that the film is attached to the stent at one end by an adhesive, by a hook and notch arrangement, or by dry heat sealing. The polymer can also be attached to the stent by wrapping the film circumferentially around the stent and attaching the polymer film to itself to form a sleeve around the stent by heating and melting the film to itself, adhesive bonding, solvent bonding, or by mechanical fastening, such as by a clip. The film may be loaded or coated with a therapeutic agent.

U.S. Pat. No. 5,628,788, issued to Pinchuk, discloses a process of melt-attaching a graft to a stent by disposing a layer of material between the stent and graft which has a lower melting point than the graft, and heating the assembly to the melting point of the low-melting point material. Pinchuk also teaches adhering a textile graft to a stent by coating a stent with vulcanizing silicone rubber adhesive and curing the adhesive. Pinchuk discloses a similar stent-graft assembly in European Patent Application EP 0 689 805 A2 and teaches that the graft member can be bonded to the stent member thermally or by the use of adhesive agents.

Similarly, World Intellectual Property Organization Application No. WO 95/05132 discloses a stent with and inner and/or an outer liner wrapped around the stent to form a seam, with the liner(s) affixed using an adhesive or melt-attached using a layer of a material with a lower melting point.

U.S. Pat. No. 5,645,559, issued to Hachtman, et al., discloses a multiple layer stent-graft assembly comprising a first layer defining a hollow tubular construction, a second layer having a self-expanding braided mesh construction and a layer of polymeric material disposed between the first and second layers. The polymeric material may be adhered by two-sided adhesive tape. The self-expanding braided mesh, the tubular material, or both may be larger in diameter in the distal regions than in the medial region.

U.S. Pat. No. 5,534,287, issued to Lukic, discloses methods which result in a covered stent, the covering adhered via a lifting medium.

U.S. Pat. No. 5,674,241, issued to Bley, et al. teaches that a hydrophilic polymer layer may be laminated, embedded, coated, extruded, incorporated, or molded around an expandable mesh stent while the stent is in its collapsed condition, and the stent and graft permitted to expand upon hydration.

European Patent Application No. EP 0 775 472 A2 discloses a PTFE-covered stent. The stent can be covered by diagonally winding an expanded PTFE tape under tension around an at least partially expanded stent.

Challenges arising in the art which none of the prior art adequately addresses include achieving a stent-graft assembly of sufficiently small crossing profile and which is sufficiently flexible. Other challenges include minimizing, if not eliminating, migration of the stent, graft or stent-graft; minimizing, if not eliminating, delamination of the stent and graft material; and minimizing thrombogenic potential, vessel reocclusion and tissue prolapse following deployment. Shortcomings associated with the prior art include: assemblies with undesirably large crossing profiles; assemblies with insufficient flexibility; inadequate adhering of coatings and coverings to stents; inadequate adhering of coatings to coverings; failure to shield the injured vascular surface; failure to prevent tissue ingrowth from occluding the lumen; failure to minimize the embolization of particles loosely adherent to the vessel wall (especially during device placement and deployment); and increased thrombogenic potential arising from delamination of the stent and graft material.

SUMMARY OF THE INVENTION

The present invention and its varied embodiments address several problems associated with the prior art. It is a first objective of this invention to provide an improved stent-graft assembly for the repair and support of a body lumen. It is a second objective of this invention to provide an improved stent-graft assembly with ample radial strength and minimal thrombogenic potential without appreciably increasing the profile of the device over that of the stent alone. Further, the decreased profile following deployment may reduce the thrombogenic potential of the device. It is a further objective of this invention to provide a thin-walled stent-graft with both ample radial strength and ample flexibility.

It is a further objective of this invention to solve the problem in the prior art of inadequate adhesion between the stent and graft material.

An additional objective of this invention is to balance the need for some tissue in-growth against the need to minimize thrombogenic potential and excessive cell growth through the interstices of the stent. This objective is achieved by providing a non-thrombogenic, thin-walled stent-graft assembly which is a smoother device, especially in regions where the prior art stent-graft has a tendency to fray, delaminate, or exhibit a scissoring effect. This objective is also achieved by providing a thin-walled stent-graft assembly which shields the injured vascular surface, controls excessive tissue in-growth through the stent, and minimizes the embolization of particles loosely adherent to the vessel wall especially during placement and deployment of the device. The device can also be used to control the luminal protrusion of dissection planes created during PTA or spontaneous fissuring.

A stent-graft assembly according to the present invention first comprises a generally cylindrical stent which comprises at least one support member. Some or all of the support member or members comprise a coating which substantially encapsulates the coated support member or members. Further, the stent-graft includes an ultra-thin membrane or covering which is attached to the coating.

In one embodiment, the proximal and distal regions of the stent-graft have an additional coating over the first coating and the membrane. In an alternative embodiment, the proximal and distal regions of the stent may be left completely uncoated and uncovered if needed for the particular medical application of the device.

The thin membrane may be either on the inner or the outer surface of the stent or both. The material used for the membrane comprises an ultra-thin polymer. In use, the membrane may have varying degrees of distensibility depending upon the desired application of the device. The membrane is bound to the coating either as a result of defining a homogeneous material with the coating or as a result of extensions of the coating into the pores of the membrane and the resulting interlocking engagement between the coating extensions and the pores of the membrane to form a composite. An alternative embodiment of the invention comprises a stent with either a continuous membrane or more than one membrane on the interior and on the exterior of the stent, the membranes bound to one another through the interstices of the stent. The membrane(s) may be sintered or otherwise bound to itself or to one another. The invention also contemplates the use of a coating at the proximal and distal regions of the stent, which substantially encapsulates the assembly at the proximal and distal regions.

The method according to a first embodiment of the present invention comprises helically wrapping ultra-thin polymeric tape around a mandrel, adjusting the angle of orientation of the tape to the mandrel depending upon the desired distensibility of the membrane and allowing adjacent edges of the helical wrapping to overlap somewhat; sintering the tape to itself over the mandrel to produce a thin tube; removing the thin tube from the mandrel; coating a stent with a polymer; covering and/or lining the coated stent with the thin tube; introducing a solvent to attach the coating to the membrane; curing the assembly to drive off remaining solvent.

The method according to an alternative embodiment comprises winding the polymeric tape around the mandrel to form two layers, in each layer reversing the angle of orientation of the tape to the longitudinal axis of the mandrel to form a bias ply, and then following the remaining steps of the method described above. In any given embodiment, the angle of orientation of the tape to the longitudinal axis of the mandrel, dependent on the width of tape and diameter of the mandrel, can be varied depending upon the desired distensibility of the graft component of the device. The sintering parameters can also be varied to affect the distensibility of the device. Further, pressure may be utilized in conjunction with sintering to improve the adherence of the tape. And finally, the amount of overlap between adjacent edges of tape can be varied depending upon the particular indication for the device.

In yet a further embodiment of a method according to the invention, a thin-walled stent-graft assembly, having inner and outer membranes, can be fabricated utilizing pressure and heat.

In any of the methods according to the particular embodiment, the extent that the coating and membrane cover the stent can be varied. And the manner in which the membrane is wrapped about the mandrel, specifically, helically or otherwise. Also according to the particular embodiment, the proximal and distal regions of the stent-graft assembly may be coated a second or multiple times to seal the resulting layers of stent, coating and membrane, and to substantially increase bond strength due to the increased surface area of the encapsulation of the stent strut.

BRIEF DESCRIPTION OF THE DRAWINGS

FIGS. 4A and 4B illustrate a cross-sectional view of an embodiment of the invention taken along line A—A of FIG. 2.

FIGS. 5A–5D respectively illustrate the sequential results of the steps of a method according to one embodiment of the present invention.

FIGS. 6A and 6B show a cross-sectional view of the device taken along line A—A of FIG. 2 of an alternate embodiment of the present invention.

FIGS. 7A–7D respectively illustrate the sequential results of the steps of a method according to one embodiment of the present invention.

FIG. 8 illustrates a perspective view of a partial progressive cut-away of an alternative embodiment of the invention.

FIG. 9 illustrates a perspective view of a partial progressive cut-away of yet another embodiment of the invention.

DETAILED DESCRIPTION OF THE PREFERRED EMBODIMENTS

Figure 1:
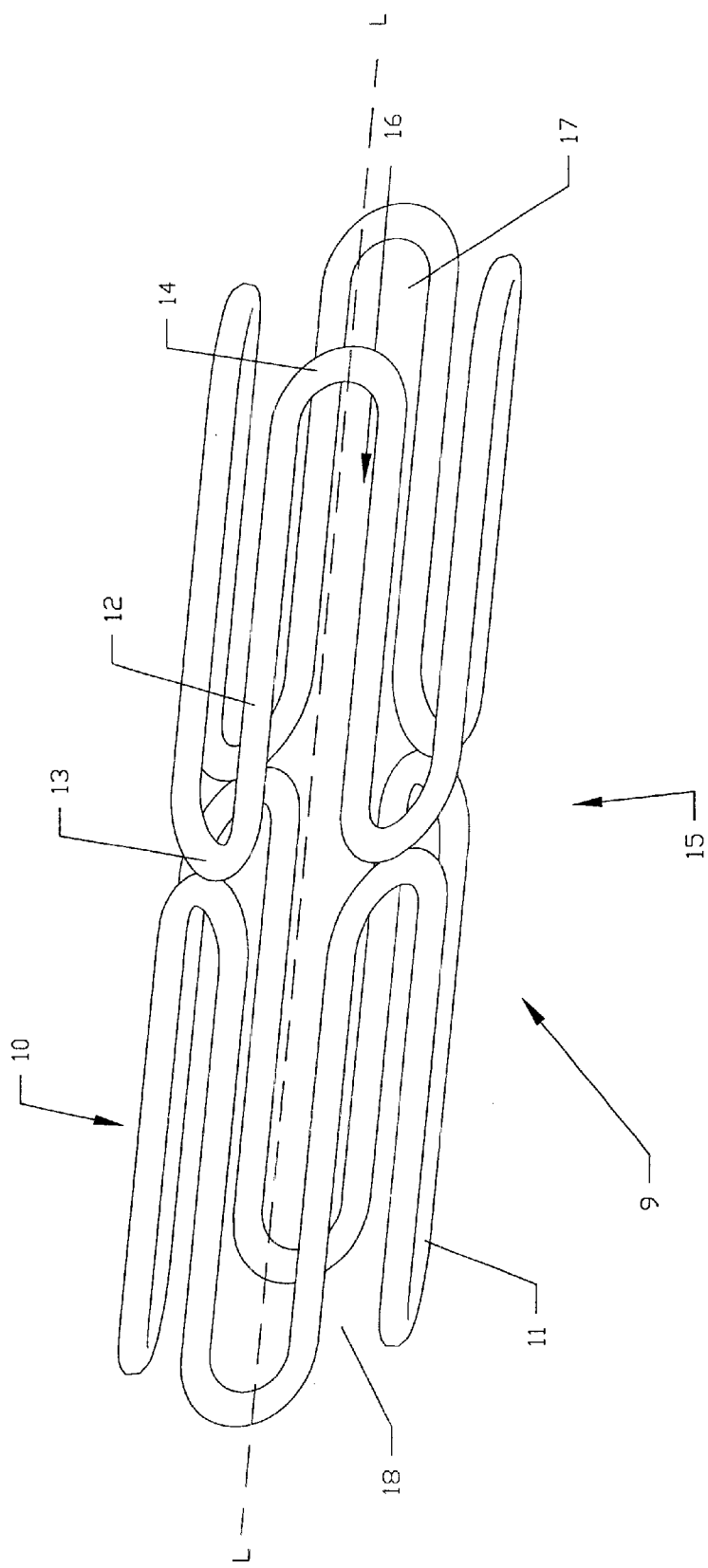
FIG. 1 illustrates a perspective view of a suitable stent for use in the present invention.
Figure 2:
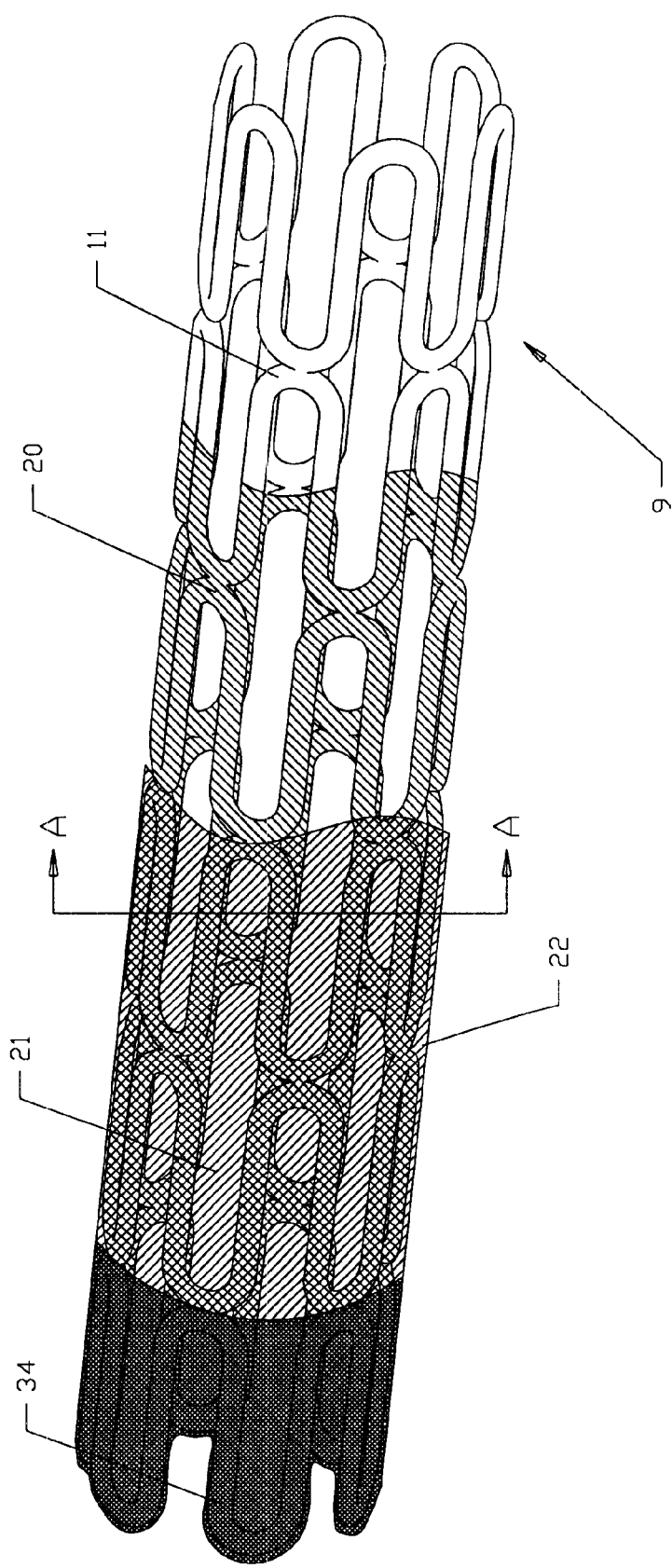
FIG. 2 illustrates a perspective view with a progressive partial cut-away of an embodiment of the stent-graft assembly according to the present invention.

The thin-walled stent-graft assembly according to the present invention is shown in FIG. 2. One recommended stent for use as the stent member according to the present invention is shown at stent (9) in FIG. 1. Other stents, such as those disclosed in U.S. Pat. No. 4,733,665 issued to Palmaz, U.S. Pat. No. 5,195,984 issued to Schatz, or U.S. Pat. No. 5,514,154 issued to Lau may also be suitable for use in the stent graft assembly.

Stent (9) is shown in FIG. 1 to include a series of connected, individual sinusoidal-shaped stent elements (10). Each individual element is similar in design and construction to the endovascular support device disclosed in U.S. Pat. No. 5,292,331 issued to Boneau, the disclosure of which is herein incorporated by reference thereto. For the purpose of further illustration, however, the series of adjacent rings or circumferential wires form support members, such as is shown for the purpose of illustration at support member (11). Each ring is formed to include a serpentine shape which includes a plurality of peaks and struts extending longitudinally between adjacent peaks, such as is shown for example at strut (12) which extends between peaks (13,14). Each ring is further connected to an adjacent ring in at least one location where the peaks of their serpentine shape meet, resulting in an interconnected series of stent elements which forms generally cylindrical body (15). Cylindrical body (15) further forms a prosthesis passageway (16) extending through the plurality of adjacent, serpentine-shaped rings along longitudinal axis L and between proximal prosthesis port (17) and distal prosthesis port (18).

Further to the interconnected series of stent elements and their respective wire-like support members which form cylindrical body (15) as shown in FIG. 1, spaces remain along cylindrical body (15) between adjacent peaks of each shaped ring and also between adjacent rings, particularly where the individual peaks of adjacent rings extend away from each other relative to longitudinal axis L.

Turning now to FIG. 2, a stent-graft assembly according to one embodiment of the present invention comprises a stent (9) having a coating (20) on some or all of the support members (11). The stent-graft assembly further comprises a thin membrane (21) which in this embodiment defines a vascular surface (22), but which in alternate embodiments may form a luminal surface or both a vascular and luminal surface. The membrane is less than 0.040 inch in thickness, and preferably is 0.00016 inch thick or less, and is distensible over a range of between 7 and 100 per cent over its primary unstretched diameter. Suitable material for the membrane may be synthetic and is preferably expanded polytetrafluoroethylene (ePTFE), but may include but is not limited to polyesters, polyurethane and silicone.

The proximal and distal regions may comprise a second coating (34), as illustrated on the distal region only in FIG. 2. Suitable material for the coating includes but is not limited to polyurethane, fluorinated ethylene propylene, and silicone. A therapeutic agent or radiopaque marker may be incorporated into the second coating or the membrane using a number of different techniques known in the art, including loading, coating or laminating.

Figure 3A:
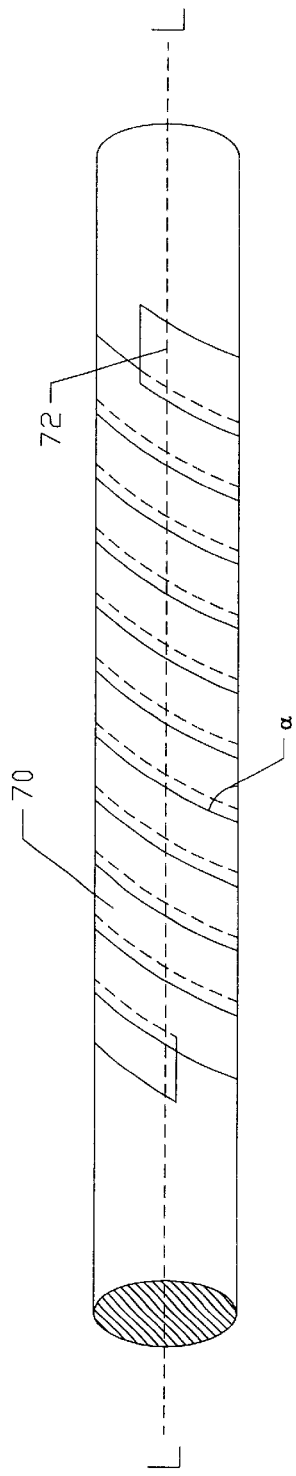
FIGS. 3A–3C illustrate a portion of the method of preparation of the membrane component of an embodiment of the stent-graft assembly according to the present invention.
Figure 3B:
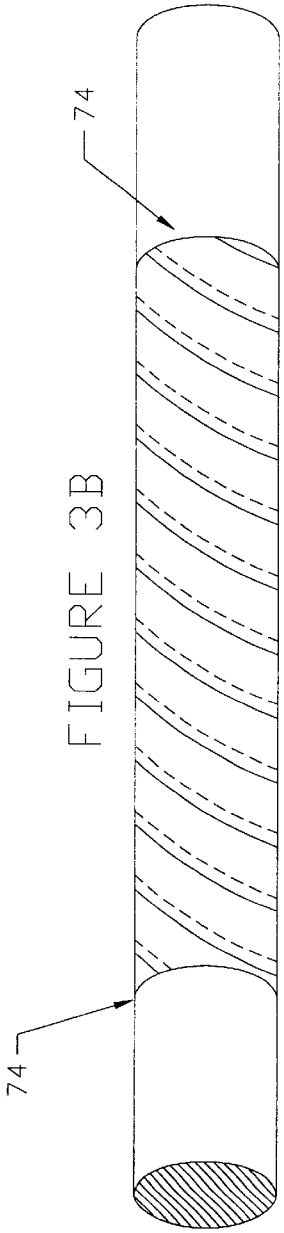
Figure 3C:
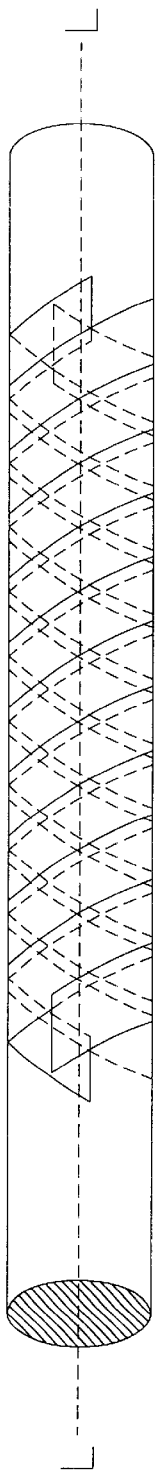

A portion of the method of preparation of the thin-walled graft component is illustrated in FIGS. 3A and 3B. Successive helical windings (70) of the thin polymeric tape (0.010 inches in thickness or less) (72) overlap to a desired extent. The amount of overlap can be varied depending upon the width of the tape, diameter of mandrel and the angle of the tape to the longitudinal axis of the mandrel. The invention contemplates that the adjacent edges of the tape overlap between 5 and 90 per cent of the width of the tape, with 10 to 60 per cent preferred. The finished graft component is distensible over a varying range depending upon the angle a of the tape to the longitudinal axis of the mandrel L. The lesser the angle $\alpha$, the greater the radial distensibility. The degree of distensibility is also affected by the sintering process, and the parameters followed to achieve sintering of the tape may be varied depending upon the desired radial distensibility. The tape can be wound at any desired angle $\alpha$ to the longitudinal axis of the mandrel, more specifically, $\alpha \leq 90°$. But in this embodiment the angle is preferably between 30 and 60 degrees. The tape is wound beginning from one end of the mandrel progressively to the other end of the mandrel. It can then be wound a second time in the reverse direction if an additional layer of polymeric tape is desired, such as shown in FIG. 3C.

The wrapped mandrel is then subject to a sufficient temperature for a sufficient time to sinter the overlap layers together. For example, a PTFE wrapped mandrel is subject to a temperature of approximately 370 degrees C. for between 30 and 45 minutes to sinter the overlapping portions together. Pressure may be utilized in conjunction with sintering to improve the adherence of the tape windings to one another.

An alternative sintering method for forming the thin-walled tube utilizes a radial compression process such as, hot isostatic compression. A preferred embodiment of which comprises placing the wrapped mandrel into a vial which is packed in a media such as, silica or other microbeads. A plunger is placed and held within the vial under pressure. The vial containing the wrapped mandrel under pressure is then heated at sufficient time and temperature to achieve sintering. As illustrated in FIG. 3B, after sintering, the ends (74) of the newly formed tube are trimmed. Moreover, with respect to the use of non-PTFE tape, rather than sintering, the tape could be solvent bonded, UV bonded or the overlapping portions could be bonded together through the use of a pressure-sensitive adhesive.

The thin tube is then removed from the mandrel. If, because the tube constricts to some degree during sintering, difficulty is encountered in removing the tube from the mandrel, several methods to facilitate removing the tube may be used. Compressed air may be discharged at one end of the tube between the tube and the mandrel, or a flat tool may be used to loosen any temporary adhesion between the mandrel and the tube. Alternatively, a collapsible mandrel or a bar of reducible diameter may be used. Also, a lubricant such as silicone, can be introduced to facilitate removal of the tube from the mandrel.

The entire stent-graft assembly can also be fabricated in accordance with method for producing the thin-walled tube utilizing pressure and heat as discussed above. Specifically, a first tape is wrapped about the mandrel. Next, the stent is loaded onto the mandrel over the first tape. A second tape is then wrapped over the stent. The entire assembly is then placed into a vial which is packed with microbeads. The assembly is then subjected to pressure and heat for a sufficient time and at a sufficient temperature to achieve sintering. Additionally, rather than placing the assembly in a microbead-filled vial, the membranes of the assembly may be sintered together by placing the assembly in an oven at approximately 370° C.

In the embodiment of the invention shown in FIGS. 4A and 4B, the materials comprising both the coating (20) and the thin-walled membrane (21) are typically of chemically similar materials, preferably polyurethanes, such that when the assembly is subjected to a solvent, the coating and thin-walled membrane partially dissolve. The solvent can be introduced via a vapor deposition process. The assembly can be placed in an enclosed chamber with a super-saturated atmosphere of solvent. At the plurality of points at which they are in contact, the coating and thin-walled membrane dissolve together to form bonding regions in which the coating and thin-walled membrane become a homogeneous material. In other words, the coating and thin-walled membrane unite to define a unitary structure (24). Although a non-porous thin-walled membrane is depicted in FIGS. 4A through 5d, the thin-walled membrane may be porous. Suitable solvents include any solvent which will degrade, dissolve or decrease the viscosity of the coating. Particularly suitable solvents include but are not limited to dimethyl acetamide, xylene, and isopropanol.

In a preferred embodiment of the invention shown in FIGS. 6A through 7D, the thin-walled membrane comprises a plurality of pores (32). When the assembly is subjected to an appropriate solvent, the coating becomes decreasingly viscous. Subject to the ratio of the solvent to the coating and the relative porosity of the thin-walled membrane, the coating in this embodiment infiltrates the pores of the thin-walled membrane to a varying extent. A plurality of bonding regions (26) at and beyond the surface of the thin-walled membrane are formed where the coating fills the pores of the thin-walled membrane and, after the assembly is cured to drive off the solvent, sealingly engages the thin-walled membrane to the coating.

The stent is coated via either a dipping process or a spraying process. In one embodiment, the spraying process is performed utilizing a 5.0% solids solution polyurethane in dimethyl acetamide. The newly coated stent is then cured to remove solvent. The sequential results of the steps for attaching the coating to a non-porous graft according to a first method of forming the thin-walled stent-graft is shown illustratively in FIGS. 5A–5D. A cross-section of the resulting structure is illustrated in FIG. 4B. FIGS. 6A and 6B, and FIGS. 7A–7D illustrate the results of the method when utilizing a porous material for the thin-walled membrane.

Further illustrating the method when utilizing a porous thin-walled membrane, following curing, the coated stent is expanded to an intermediate diameter, such as by loading it onto an expansion mandrel, and the thin polymeric tube (21) is mounted over the exterior of the coated stent, a cross-sectional representation of which is shown in FIGS. 7B and 7C. The method could have either the alternative step or the added step of placing a tube within the stent prior to applying the solvent, such that the resulting assembly has a thin-walled membrane on the interior of the stent or on both the interior and the exterior of the stent.

The assembly is then subjected to a solvent, such as dimethyl acetamide, which will decrease the viscosity of the coating and cause it to migrate into the pores of the thin-walled membrane. The assembly is then cured in a forced air oven to remove any remaining solvent. The resulting bond is characterized in FIGS. 6A, 6B and 7D, showing a cross-section of a support member (11) encapsulated in coating, and the coating (20) extending into the pores of the graft member or thin-walled membrane (21) such that the coating and thin-walled membrane are in interlocking engagement with one another. Following the removal of solvent, the device is configured to its insertion diameter.

FIG. 8 represents a partial progressive cut-away of another embodiment of the invention. In the embodiment illustrated in FIG. 8, the assembly comprises a stent (60), a first thin membrane (62) defining a lumenal surface, a second thin membrane (64) defining a vascular surface and a coating (65). Because FIG. 8 is a progressive cut-away illustration, the coating is illustrated as substantially encapsulating the distal region (68) of the assembly only, but in actuality encapsulates both the proximal and the distal regions. The thin-walled membranes may be sintered or otherwise bonded to one another through the interstices of the stent. The coating is bonded to the thin-walled membranes in the same manner as in the previous embodiments.

FIG. 9 illustrates yet another embodiment of the invention, as a perspective view of a progressive partial cut-away of this additional embodiment. In the embodiment depicted in FIG. 9, the stent (9) comprises a coating (20) substantially covering all of the support member or members (11). The device further comprises a thin membrane (21) which in this embodiment defines a vascular surface (22). The thin membrane (21) is sized such that it covers the coated stent up to the last stent element (10) on each end of the stent (9), as shown in FIG. 9. Although, the membrane may alternatively extend up to and cover at least a portion of the last stent element. The device further comprises a second coating (34) which covers the last stent element (10) and at least a portion of the second to last stent element at both the proximal and distal regions of the assembly, although illustrated only at the distal region in FIG. 9.

EXAMPLE 1

For the purpose of further illustration, an exemplary method for preparing a thin-walled stent-graft assembly is described as follows. A thin tape of ePTFE, approximately 0.0004 inch in thickness, was wound around a 3.25 mm mandrel under slight tension at approximately a 60 degree angle to the longitudinal axis of the mandrel. Adjacent edges of the tape overlapped approximately 67 per cent of the tape's width. The wrapped mandrel was sintered at 370 degrees Celsius for 45 minutes.

A GFX stent, which is manufactured by Arterial Vascular Engineering, Inc., in Santa Rosa, Calif., was provided in a 18 mm length. The end of the stent was mounted on a 0.109 inch diameter mandrel. The stent was pre-heated at 80 degrees Celsius. The stent was then sprayed at a rate of 6.3 microliters per second for 10 seconds with a 5.0% solids solution of polyurethane in dimethyl acetamide. The coated stent was then cured for 90 seconds at 100 degrees Celsius. The procedure was repeated with the opposite end of the stent mounted on the mandrel.

Polyurethanes which may be used in accordance with the present invention include segmented polycarbonate polyurethane such as that sold under the trademark CHRONOFLEX type AR, which is available from Cardiotech, Inc., located in Woburn, Mass.

The thin ePTFE tube was removed from the mandrel and placed over the coated stent. The stent was then expanded to a 3.5 mm diameter over an expansion mandrel while inside the thin tube previously prepared, such that the stent was well opposed to the graft wall. The stent and graft combination were then placed in a super-saturated atmosphere of dimethyl acetamide within an enclosed chamber. The device was then cured in a forced air oven at 80 degrees C. for fifteen minutes. Following curing, the ends of the stent-graft were trimmed to remove graft material from between the peaks of the support members. The stent was then configured to its insertion diameter. Utilizing a fine-tipped syringe dispenser, a small drop of 5% polyurethane solution was placed on each stent peak to fully encapsulate the stent member at the peak. The assembly was again cured for thirty minutes at 80 degrees Celsius.

EXAMPLE 2

Utilizing a thin, expanded polytetrafluoroethylene tape of approximately 0.0004 inch in thickness, the tape was wound helically around a mandrel from one end of the mandrel and progressing to the other end under slight tension at an angle of approximately 50 degrees to the longitudinal axis of the mandrel. The tape was wound a second time in the opposite direction to form a second layer, again at an angle of approximately 50 degrees to the longitudinal axis of the mandrel. Throughout each step of wrapping the tape, adjacent edges of the tape overlapped approximately 30 per cent. The wrapped mandrel was then sintered at a temperature of 370 degrees Celsius for forty-five minutes.

A GFX coronary bypass stent, which is manufactured by Arterial Vascular Engineering, Inc., was spray coated with five microliters per second for five seconds with segmented polycarbonate polyurethane. The process was performed with the end of the stent mounted on a mandrel, repeated an additional five times, each time alternating the end of the stent which was exposed to the spray. Between each coat, the stent was cured for five minutes in a forced air oven at 80 degrees C. The coated stent was then cured in a forced air oven at 80 degrees Celsius for one hour, and allowed to cool.

The thin ePTFE tube was removed from the mandrel and placed over the coated stent. The coated stent was then expanded within the prepared thin ePTFE tube on an expansion mandrel to 4.5 mm. The coated stent with graft were then exposed to dimethyl acetamide solvent via an atomizing spray for one second at a rate 100 microliters per second at 10 second intervals within an enclosed chamber at ambient temperature for 30 minutes.

The assembly was then cured at 80 degrees Celsius in a forced air oven for 30 minutes. Following curing, the ends of the stent-graft were trimmed to remove graft material from between the peaks of the support members. The stent was then configured to its insertion diameter.

A stent-graft assembly having a thin-walled membrane and method of manufacturing the same have been disclosed. Although the present invention has been described in accordance with the embodiments shown, one of ordinary skill in the art will readily recognize that there could be variations to the embodiments and those variations would be within the spirit and scope of the present invention.

A wide variety of suitable materials used for stents and grafts may be interchanged without diverging from the methods or structures of the invention claimed. For example, the type of stent utilized could be varied greatly. The embodiments disclosed herein focus on a stent comprising independent support members, but a stent which is comprised of a slotted tube or of a rolled film configuration may also be used. Further, suitable stents include stents made of nitinol or other shape memory alloy. In order to confer radiopacity on an alternative stent, various methods may be utilized. For example, a radiopaque metal marker such as Gold, Tantalum, Platinum, Iridium or any alloy thereof may be embedded or encapsulated into the coating of the device.

A further example of yet another manner of fabricating the stent-graft assembly involves wrapping a first tape about the mandrel. Loading the stent onto the mandrel over the first tape. Wrapping a second tape over the stent. And then applying a hot shoe proximate the interstices between the stent support members to sinter the two layers of tape together.

Suitable membrane material also may include autographs, which are vessels transplanted within the patient or host; allografts, which refer to vessels transplanted from a donor which is a member of the same species as the patient or host; or xenografts, which are transplanted from a donor which is not a member of the same species as the patient or host.

Further, the instant invention can also be used for indications other than repairing and/or providing radial support to a body lumen. Other examples include aneurysm isolation and vessel occlusion. The foregoing embodiments and examples are illustrative and are in no way intended to limit the scope of the claims set forth herein.

We claim:

1. A stent-graft assembly comprising:

a generally cylindrical stent comprising at least one support member, an exterior and an interior, a medial region, a proximal region and a distal region, said at least one support member defining a passageway through the stent;

at least one membrane, said at least one membrane affixed to at least a portion of at least one of said interior and exterior, wherein the at least one membrane defines at least one of a luminal surface and a vascular surface, said at least one membrane being less than 0.001 inch thick.

2. The stent-graft assembly according to claim 1 wherein the at least one membrane is of generally uniform thickness.

3. The stent-graft assembly according to claim 1 wherein the stent further comprises:

a first polymeric coating substantially encapsulating at least a portion of the at least one support member; wherein
the at least one membrane is porous and is affixed to the coating, and;
the coating extends into the pores of the membrane to securely engage the membrane.

4. The stent-graft assembly of claim 3 wherein the assembly also comprises a second coating at the proximal and distal regions of the assembly.

5. The stent-graft assembly of claim 4 wherein the second coating substantially encapsulates the exterior and the interior or the at least one membrane at the proximal and distal regions of the assembly.

6. The stent-graft assembly of claim 3 wherein the coating is a polymer selected from the group consisting of polyurethane, flourinated ethylene propylene and silicone.

7. The stent-graft assembly according to claim 1 wherein the assembly also comprises a coating at the proximal and distal regions of the assembly.

8. The stent-graft assembly according to claim 7 wherein the coating substantially encapsulates the exterior and the interior of the at least one membrane at the proximal and distal regions of the assembly.

9. The stent-graft assembly of claim 1 wherein said at least one membrane is a polymer selected from the group consisting of polyurethane, polytetrafluoroethylene, dimethyl terephthalate, polyester, polyethylene terephthalate and silicone.

10. The stent-graft assembly of claim 1 wherein the at least one support member comprises:

at least one stent element formed of a plurality of substantially straight segments and configured to provide a plurality of upper and lower peaks; and the at least one stent element being capable of retaining a compressed configuration while mounted onto an outer surface of a catheter for delivery to an affected area of a vessel until application of an outward radial force to form an expanded configuration.

11. The stent-graft assembly of claim 1 wherein the membrane comprises a primary diameter and wherein the membrane is distensible over a range of between 7 and 100% beyond the primary diameter.

* * * * *